(12) United States Patent
Gurjar et al.

(10) Patent No.: US 8,921,596 B2
(45) Date of Patent: Dec. 30, 2014

(54) PROCESS FOR THE PREPARATION OF MELPHALAN HYDROCHLORIDE

(75) Inventors: Mukund Keshav Gurjar, Pune (IN); Narendra Kumar Tripathy, Pune (IN); Sandeep Anilrao Kotharkar, Pune (IN); Pradip Nana Patil, Pune (IN); Samit Satish Mehta, Pune (IN)

(73) Assignee: Emcure Pharmaceuticals, Ltd., Pune (IN)

( * ) Notice: Subject to any disclaimer, the term of this patent is extended or adjusted under 35 U.S.C. 154(b) by 830 days.

(21) Appl. No.: 13/048,783

(22) Filed: Mar. 15, 2011

(65) Prior Publication Data

US 2012/0116117 A1    May 10, 2012

(30) Foreign Application Priority Data

Nov. 4, 2010   (IN) .......................... 3062/MUM/2010

(51) Int. Cl.
  *C07C 229/00*  (2006.01)
  *C07C 227/18*  (2006.01)
(52) U.S. Cl.
  CPC .................................. *C07C 227/18* (2013.01)
  USPC ....................................................... 562/443
(58) Field of Classification Search
  CPC ............................ C07C 227/18; C07C 229/42
  USPC ....................................................... 562/443
  See application file for complete search history.

(56) References Cited

U.S. PATENT DOCUMENTS

| 3,032,584 A | 5/1962 | Bergel |
| 3,032,585 A | 5/1962 | Bergel |
| 4,997,651 A * | 3/1991 | Poole et al. ................... 514/564 |

FOREIGN PATENT DOCUMENTS

| DE | 1292660 B | 4/1969 |
| EP | 233733 A2 | 8/1987 |
| FR | 1360836 A | 5/1964 |
| GB | 1064972 A | 4/1967 |
| GB | 1377336 A | 12/1974 |
| RO | 57195 A2 | 9/1974 |

OTHER PUBLICATIONS

Fetzer, WR, Determination of Moisture by Distillation, Anal. Chem. 1951, 23(8), 1062-1069.*

* cited by examiner

*Primary Examiner* — Fereydoun G Sajjadi
*Assistant Examiner* — Kofi Adzamli
(74) *Attorney, Agent, or Firm* — William D. Hare, Esq.; McNeely, Hare & War, LLP

(57) ABSTRACT

The present invention provides a simple and efficient method for synthesis of 4-[bis(2-chloroethyl)-amino]-L-phenylalanine hydrochloride. The process involves the treatment of 4-[bis(2-chloroethyl)-amino]-L-phenylalanine free base with hydrochloric acid in water followed by isolation of 4-[bis(2-chloroethyl)-amino]-L-phenylalanine hydrochloride of desired purity.

17 Claims, 2 Drawing Sheets

Formula I

SCHEME I

US 8,921,596 B2

PROCESS FOR THE PREPARATION OF MELPHALAN HYDROCHLORIDE

FIELD OF THE INVENTION

The present invention relates to a process for preparation of melphalan hydrochloride. More specifically, the invention relates to a method for preparation of melphalan hydrochloride by reaction of melphalan free base with hydrochloric acid in water, and isolating melphalan hydrochloride of Formula I having desired purity.

BACKGROUND OF THE INVENTION

Melphalan, chemically known as 4-[bis(2-chloroethyl)amino]-L-phenylalanine and also by other names like L-phenylalanine mustard, L-sarcolysine or L-PAM is a bi-functional alkylating agent that acts against selected human neoplastic diseases and is the L-isomer of 4-[bis(2-chloroethyl)amino]-phenylalanine, which exhibits superior anti-tumor activity than medphalan (D-isomer) and sarcolysine (DL-isomer). Melphalan is marketed as its hydrochloride salt, under the brand name 'Alkeran®' by The Wellcome Foundation.

Various researchers have attempted to synthesize the active hydrochloride salt of the L-form of 4-[bis(2-chloroethyl)amino]-phenylalanine. The synthesis of melphalan was first disclosed in U.S. Pat. No. 3,032,584 and U.S. Pat. No. 3,032,585 wherein melphalan free base is prepared by a synthetic route which employs a phthalimide functional group for protecting the glycine amino functional group. However, these and the subsequent patents GB 1,377,336 and EP 233 733, do not disclose a method for isolating the acid addition salts of the L-form of 4-[bis(2-chloroethyl)-amino]-phenylalanine, specifically the hydrochloride salt.

U.S. Pat. No. 4,997,651 discloses a method for preparing melphalan hydrochloride comprising addition of hydrochloric acid to a slurry of melphalan free base in an alcohol, preferably ethanol and refluxing the mixture for minimum duration to reduce the level of impurities. The present inventors have noted that complete conversion of the free base to the hydrochloride salt in a short time on a commercial scale is not practically feasible because it results in large amounts of unreacted material. Further, an extended duration of heating in alcohols was found to result in associated impurities, which required successive purifications for obtaining a product of the desired purity. Also, an additional purification step reduces the yield considerably, thereby limiting the suitability of the method to laboratory scale preparation only.

Similarly, GB 1,064,972, FR 1 360 836 and DE 1 292660 also describe the use of an alcohol for preparing the hydrochloride salt with the same disadvantages. RO 57195 describes a method for purification of melphalan free base through formation of the hydrochloride salt followed by treatment with a suitable base such as sodium bicarbonate or sodium acetate. The document is silent about isolation of hydrochloride salt. However, if one carries out the isolation, one would face the problem of associated impurities, which eventually requires extensive purification.

U.S. Pat. No. 4,997,651 and DE 1 292660 also utilize an alcoholic solution of hydrochloric acid with the same result. A replication of these prior art methods by the present inventors revealed that associated impurities were formed, thus requiring subsequent purifications. Regulatory guidelines necessitate the removal of associated impurities by purification to obtain melphalan hydrochloride of desired purity, which eventually reduces the yield.

It is clearly evident from the above prior art that the product obtained by prior art methods generate associated impurities of up to 5-8% and requires extensive purification resulting in high production cost and thereby making such process commercially unsuitable. Moreover, health authorities all over the world have very stringent norms for permissible limits of associated impurities in the final dosage formulation.

Therefore, to overcome the problems associated with prior art, there was a need to develop
i) a simple, efficient, high yielding process which does not result in unreacted starting material remaining after treatment with hydrochloric acid and
ii) a process which yields a product of desired purity with minimal impurities, thereby obviating the need for extensive purification.

SUMMARY OF THE INVENTION

The present invention relates to a method for synthesis of melphalan hydrochloride of Formula I comprising treatment of 4-[bis(2-chloroethyl)-amino]-L-phenylalanine with hydrochloric acid in water followed by isolation of melphalan hydrochloride of desired purity. The isolation may be carried out by removal of water, stirring with an alcohol and separating the obtained solid to yield 4-[bis(2-chloroethyl)-amino]-phenylalanine hydrochloride (I) of desired purity.

DETAILED DESCRIPTION OF THE INVENTION

Figure 1:
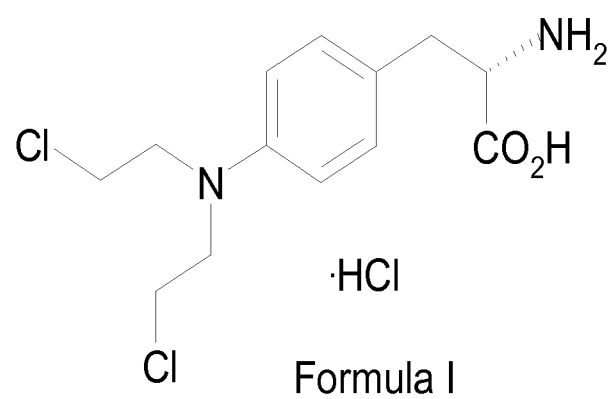
FIG. 1 shows the structural formula of the compound of Formula I, 4-[bis(2-chloroethyl)-amino]-L-phenylalanine hydrochloride.
Figure 2:
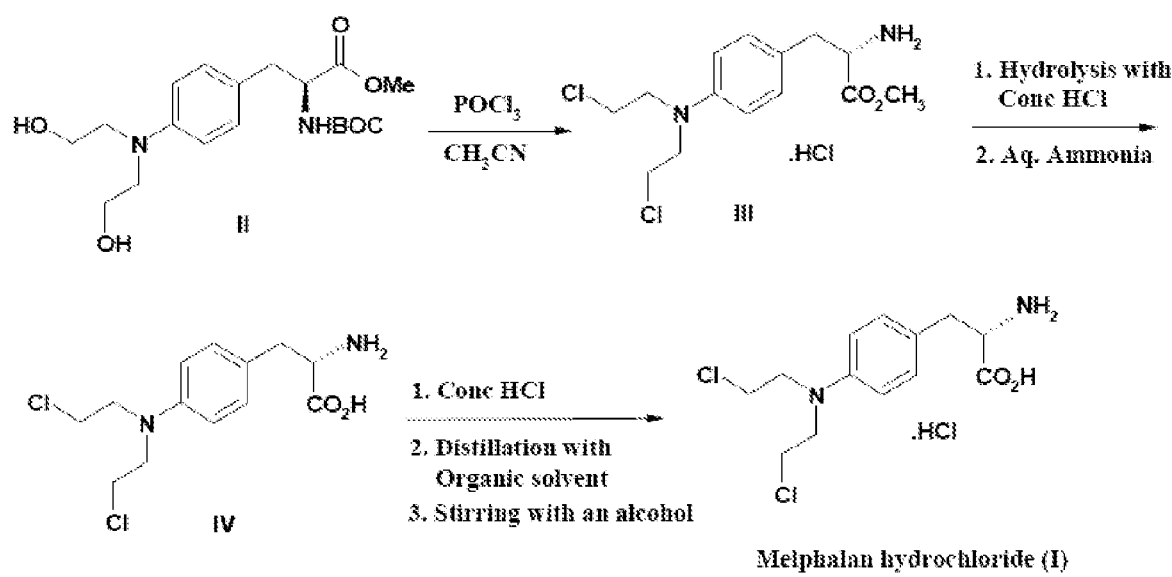
FIG. 2 shows Scheme I, a synthetic process for preparation of melphalan hydrochloride of Formula I starting from N-t-butyloxycarbonyl-bis-[(2-hydroxyethyl)-amino]-L-phenylalanine methyl ester of Formula II.

Melphalan free base is prepared by conventional methods, such as from N-t-butyloxycarbonyl-bis-[(2-hydroxyethyl)-amino]-L-phenylalanine methyl ester (II), as represented in Scheme-I (FIG. 2), which in turn may be prepared by the process disclosed in CN 101100440. N-t-butyloxycarbonyl-bis-[(2-hydroxyethyl)-amino]-L-phenylalanine methyl ester (II) is subjected to chlorination with phosphorus oxychloride or thionyl chloride, followed by acid hydrolysis for the removal of the ester protection, and neutralization with aqueous ammonia to produce 4-[bis(2-chloroethyl)-amino]-L-phenylalanine i.e. melphalan (IV) free base as represented in scheme-I.

The present inventors have found that the hydrochloride salt of melphalan can be obtained using water during treatment with hydrochloric acid and in absence of an organic solvent. Further, the isolation of the highly water miscible melphalan hydrochloride may be achieved by removal of water or by addition of an anti-solvent to precipitate the salt.

Water may be removed from the reaction mixture by freeze drying or lyophilization, or with the help of organic solvents capable of forming an azeotropic mixture with water. Examples of anti-solvents that may be used to precipitate melphalan hydrochloride include alcohols. It should be noted that such a process using water as reaction medium was not attempted in prior art.

An alcohol may be added to the residue obtained after water removal to obtain melphalan hydrochloride of desired purity, i.e. with level of impurities conforming to drug regulatory specifications. The addition of an alcohol after concentration of the reaction mixture makes the product free flowing and constitutes an inbuilt purification step as it selectively dissolves associated impurities, which are then removed during filtration. The process is convenient and cost effective for commercial scale because the process obviates the need for an additional purification step.

In one embodiment of the present invention, the reaction of 4-[bis(2-chloroethyl)-amino]-L-phenylalanine with hydrochloric acid in water is followed by concentration in presence of an organic solvent, stirring of the concentrated mixture with an alcohol, and separating the obtained solid to yield 4-[bis(2-chloroethyl)-amino]L-phenylalanine hydrochloride (I) of desired purity.

In some embodiments, aqueous hydrochloric acid is added to melphalan free base (IV) suspended in water at a temperature of about 15° C. to about 20° C. The mixture is stirred at about 15° C. to about 45° C. for 2 to 3 hours to give a clear solution containing 4-[bis(2-chloroethyl)-amino]-L-phenylalanine hydrochloride (I). In other embodiments, the acid addition salt formation reaction may be carried out between about 25° C. and about 30° C.

The isolation of the compound of Formula I may be carried out by removing water azeotropically by addition of one or more organic solvents to the reaction mixture and concentrating the mixture under reduced pressure. The addition of the organic solvent followed by concentration of the reaction mixture may be carried out more than once, if desired, to achieve lower moisture content, such as a moisture content of less than 5%.

Any organic solvent which forms an azeotropic mixture with water may be employed, such as hydrocarbons, esters, alcohols, alkyl halides and mixtures thereof. The hydrocarbon may be aromatic and selected from toluene, cumene, xylene or mixtures thereof. Alternatively, the hydrocarbon may be aliphatic, such as, cyclohexane or hexane. Examples of esters include ethyl acetate and methyl acetate. Examples of alcohol include ethanol, methanol and isopropanol. Examples of alkyl halides include methylene chloride, ethylene chloride and propylene chloride.

The residue is stirred with an alcohol at ambient temperature or at lower temperatures, such as, about 0° C. to about 5° C. It should be noted that prior to addition of alcohol, the concentrated residue may be sticky and not filterable due to the presence of impurities, which hinder the formation of an easily filterable free flowing solid. The addition of an alcohol before filtration constitutes an inbuilt purification step, and helps in dissolving impurities without affecting the yield, to obtain the compound of Formula I having desired purity. The alcohol used for isolation may be a $C_2$ to $C_6$ alcohol and may be selected from ethanol, isopropyl alcohol, n-propanol, isobutanol, t-butanol or mixture thereof.

The solid melphalan hydrochloride obtained after stirring with alcohol, or after anti-solvent precipitation is separated by conventional methods, such as, filtration, or centrifugation.

The invention is further explained with the help of following illustrative examples. However, these examples should not be construed as limiting the scope of the invention in any way.

EXAMPLES

Example 1

Preparation of 4-[bis(2-chloroethyl)-amino]-L-phenylalanine methyl ester hydrochloride (Compound of Formula III)

N-t-butyloxycarbonyl-bis-[(2-hydroxyethyl)-amino]-L-phenylalanine methyl ester (II) (85 grams, 0.222 mole) was stirred in acetonitrile (425 ml) to get a clear solution at 25° C. to 30° C. Phosphorous oxychloride (124 ml, 1.33 moles) was charged drop wise to the above clear solution at 25° C. to 30° C. and the mixture was stirred at 75° C. to 80° C. After completion of the reaction based on HPLC monitoring) the reaction mixture was concentrated under reduced pressure to give crude 4-[bis(2-chloroethyl)-amino]-L-phenylalanine methyl ester hydrochloride (III) which was used as such for the next step.

Example 2

Preparation of 4-[Bis(2-chloroethyl)-amino]-L-phenylalanine (Compound of Formula IV)

Concentrated hydrochloric acid (425 ml, 5 volume) was added to the crude 4-[bis(2-chloroethyl)-amino]-L-phenylalanine methyl ester hydrochloride (III) obtained in Example 1 and the reaction mixture was heated at 80° C. to 85° C. After completion of the reaction, as monitored by HPLC, the mixture was treated with activated carbon and filtered through hyflo bed. The filtrate was cooled to 0° C. and the pH of the filtrate was adjusted to pH 6.0 by addition of aqueous ammonia solution (450 ml). The product was filtered, washed with water and the wet 4-[bis(2-chloroethyl)-amino]-L-phenylalanine free base (IV) was used as such for preparation of the hydrochloride salt.

Example 3

Preparation of 4-[bis(2-chloroethyl)-amino]-L-phenylalanine hydrochloride (Compound of Formula I)

4-[Bis(2-chloroethyl)-amino]-L-phenylalanine (V) obtained in Example 2 was treated with concentrated hydrochloric acid (80 ml) at 25° C. to 30° C. and stirred at the same temperature for 15-20 hours. Toluene (1060 ml) was added and the resulting mixture was concentrated under reduced pressure till the moisture content of the residue was about 5%. Isopropyl alcohol (765 ml) was added to the resulting residue and stirred at 0° C. to 5° C. for 2-4 hours. 4-[Bis(2-chloroethyl)-amino]-L-phenylalanine hydrochloride thus obtained was filtered, washed with isopropyl alcohol (340 ml) and dried under reduced pressure at 45° C. to 50° C.

Yield: 38 grams,
HPLC Purity: >99%

The invention claimed is:
1. A process for the preparation of 4-[bis(2-chloroethyl)-amino]-L-phenylalanine hydrochloride from 4-[bis(2-chloroethyl)-amino]-L-phenylalanine, comprising:
(i) treating 4[bis(2-chloroethyl)-amino]-L-phenylalanine in water with hydrochloric acid, and
(ii) isolating the obtained 4-[bis(2-chloroethyl)-amino]-L-phenylalanine hydrochloride as a solid, wherein the iso- lation is carried out by removing water by addition of an organic solvent capable of forming an azeotropic mixture with water and concentration of the resulting mixture.

2. The process of claim 1, wherein the treatment of step (i) is carried out at a temperature of about 15° C. to about 45° C.

3. The process of claim 2, wherein the treatment temperature is about 25° C. to about 30° C.

4. The process of claim 1, wherein the addition of organic solvent and concentration are repeated to obtain a mixture having moisture content below 5%.

5. The process of claim 1, wherein the organic solvent is a hydrocarbon.

6. The process of claim 5, wherein the hydrocarbon is toluene.

7. The process of claim 1, wherein the concentration is followed by addition of an alcohol and stirring.

8. The process of claim 7, wherein the alcohol is selected from the group comprising of $C_2$ to $C_6$ alcohols.

9. The process as claimed in claim 8, wherein the alcohol is selected from the group consisting of ethanol, isopropyl alcohol, n-propanol, isobutanol, t-butanol and mixtures thereof.

10. The process of claim 9, wherein the stirring is carried out at a temperature of about 0° C. to about 5° C.

11. The process of claim 9, wherein the stirring is carried out at ambient temperature.

12. The process of claim 9, wherein the stirred mixture is filtered to obtain melphalan hydrochloride having desired purity.

13. A process for the preparation of 4-[bis(2-chloroethyl)-amino]-L-phenylalanine hydrochloride from 4-[bis(2-chloroethyl)-amino]-L-phenylalanine, comprising:
   (i) treating 4-[bis(2-chloroethyl)-amino]-phenylalanine in water with hydrochloric acid;
   (ii) adding an organic solvent capable of forming an azeotropic mixture with water;
   (iii) concentrating the mixture obtained from step (ii);
   (iv) adding an alcohol to the residue obtained from step iii and stirring the mixture to obtain 4-[bis(2-chloroethyl)-amino]-L-phenylalanine hydrochloride as a solid; and
   (v) separating the obtained solid.

14. The process of claim 13, wherein the preparation of 4-[bis(2-chloroethyl)-amino]-L-phenylalanine hydrochloride from 4-[bis(2-chloroethyl)-amino]-L-phenylalanine, consists of the steps of:
   (i) treating 4-[bis(2-chloroethyl)-amino]-phenylalanine in water with hydrochloric acid in the absence of an organic solvent;
   (ii) adding an organic solvent capable of forming an azeotropic mixture with water;
   (iii) concentrating the mixture obtained from step (ii);
   (iv) adding an alcohol to the residue obtained from step (iii) and stirring the mixture to obtain 4-[bis(2-chloroethyl)-amino]-L-phenylalanine hydrochloride as a solid; and
   (v) separating the obtained solid.

15. The process of claim 13, wherein step (i) requires a temperature of about 15° C. to about 45° C., and steps (ii) and (iii) are repeated to obtain a mixture having a moisture content below 5%.

16. The process of claim 13, wherein the alcohol is selected from the group comprising $C_2$ to $C_6$ alcohols and the stirring is carried out at a temperature of about 0° C. to about 5° C.

17. The process of claim 16, wherein the alcohol is selected from the group consisting of ethanol, isopropyl alcohol, n-propanol, isobutanol, t-butanol and mixtures thereof, and the stirring is carried out at an ambient temperature.

\* \* \* \* \*